(12) United States Patent
Abboud

(10) Patent No.: US 8,845,328 B2
(45) Date of Patent: Sep. 30, 2014

(54) JAW IMPLANT

(76) Inventor: Marcus Abboud, Setauket, NY (US)

(*) Notice: Subject to any disclaimer, the term of this patent is extended or adjusted under 35 U.S.C. 154(b) by 0 days.

(21) Appl. No.: 13/401,869

(22) Filed: Feb. 22, 2012

(65) Prior Publication Data

US 2012/0219928 A1    Aug. 30, 2012

(30) Foreign Application Priority Data

Feb. 24, 2011    (EP) .................................... 11155907

(51) Int. Cl.
*A61C 8/00* (2006.01)

(52) U.S. Cl.
CPC .............. *A61C 8/005* (2013.01); *A61C 8/0068* (2013.01); *A61C 8/0053* (2013.01); *A61C 8/0069* (2013.01); *A61C 8/0075* (2013.01)
USPC .......................................... 433/173; 433/174

(58) Field of Classification Search
USPC ................ 433/172–176, 201.1; 606/301–331
See application file for complete search history.

(56) References Cited

U.S. PATENT DOCUMENTS

| | | | | |
|---|---|---|---|---|
| 4,934,935 A | * | 6/1990 | Edwards | 433/174 |
| 4,988,297 A | | 1/1991 | Lazzara et al. | |
| 5,178,539 A | * | 1/1993 | Peltier et al. | 433/173 |
| 5,577,912 A | | 11/1996 | Prins | |
| 5,727,942 A | * | 3/1998 | Hartmann et al. | 433/173 |
| 2007/0099151 A1 | | 5/2007 | Ilan et al. | |
| 2007/0281281 A1 | * | 12/2007 | Cottrell | 433/174 |
| 2008/0213728 A1 | * | 9/2008 | Rhew | 433/201.1 |
| 2009/0023109 A1 | * | 1/2009 | Jinton et al. | 433/174 |
| 2010/0129774 A1 | * | 5/2010 | Martinez et al. | 433/201.1 |
| 2010/0330529 A1 | * | 12/2010 | Shalom | 433/173 |

FOREIGN PATENT DOCUMENTS

| | | |
|---|---|---|
| DE | 199 03 482 A1 | 8/2000 |
| DE | 20 2006 012016 U1 | 11/2006 |
| DE | 10 2006 045188 A1 | 3/2008 |
| EP | 0 449 334 A1 | 10/1991 |
| WO | WO 2004/105632 A1 | 12/2004 |
| WO | WO 2008/141404 A1 | 11/2008 |

\* cited by examiner

*Primary Examiner* — Yogesh Patel
(74) *Attorney, Agent, or Firm* — Norman B. Thot

(57) ABSTRACT

A jaw-mounted dental implant with an implant body. The implant body includes an attachment fastening structure arranged in the implant body which fastens an implant attachment on an implant body longitudinal end facing away from a jaw. An attachment plane is arranged at the implant body longitudinal end facing away from the jaw and is inclined at an attachment angle β of 75° to 45° relative to an implant body longitudinal axis. A support structure projects outward from an implant body outer surface on a longitudinal end of an implant body bone portion facing away from the jaw. The support structure is formed by at least one support web arranged in a web plane. The web plane is interrupted by an interruption region arranged in a circumferential direction at an obtuse-angle side of the implant body so as to not extend around an entire circumference of the implant body.

17 Claims, 2 Drawing Sheets

_JAW IMPLANT_

CROSS REFERENCE TO PRIOR APPLICATIONS

Priority is claimed to European Patent Application No. EP 11 155 907.6, filed Feb. 24, 2011. The entire disclosure of said application is incorporated by reference herein.

FIELD

The present invention relates to a dental implant to be inserted into the jaw for support of an implant attachment.

BACKGROUND

A dental implant for insertion into the jaw is defined as that part of a dental implant assembly which is implanted directly into the patient's jaw to support an implant attachment. The implant attachment normally consists of a replacement-tooth neck portion and a separate replacement-tooth head portion, the so-called tooth crown.

Generally, the overall implant assembly is desired to have a linear configuration, i.e., the jaw-mounted dental implant and the implant attachment are arranged approximately on the same longitudinal axis. However, the patient's jawbone, the nerve tracts extending therein and other marginal conditions will not always allow the jaw-mounted dental implant to be implanted into the jawbone substantially transversely to the occlusal plane. If the jaw-mounted dental implant is implanted at an inclination relative to the occlusal plane, the implant attachment must be fixed to the jaw-mounted dental implant at a corresponding inclination.

A dental implant assembly comprising an implant attachment inclined relative to the jaw-mounted dental implant is described in EP 0 449 334 A1. A problem in inclined implant attachments resides in the non-axial introduction of force into the jaw-mounted dental implant, which, due to the resulting high rotational moments, leads to high radial forces which will be transmitted to the jawbone nearly in a punctiform manner. In these regions, there will thus exist a high likelihood of bone deterioration, resulting in a further degradation of the anchoring of the dental implant in the patient's jaw.

SUMMARY

An aspect of the present invention is to provide a jaw-mounted dental implant for an inclined and respectively bent arrangement of the implant wherein an improved support in the patient's jaw is obtained.

In an embodiment, the present invention provides a jaw-mounted dental implant with an implant body. The implant body includes an attachment fastening structure arranged in the implant body. The attachment fastening structure is configured to fasten an implant attachment on an implant body longitudinal end facing away from a jaw. An attachment plane facing away from the jaw is arranged at the implant body longitudinal end facing away from the jaw. The attachment plane is inclined at an attachment angle $\beta$ of 75° to 45° relative to an implant body longitudinal axis. A support structure projects outward from an implant body outer surface on a longitudinal end of an implant body bone portion facing away from the jaw. The support structure is formed by at least one support web arranged in a web plane. The web plane is arranged substantially parallel to the attachment plane. The at least one support web is interrupted by an interruption region arranged in a circumferential direction at an obtuse-angle side of the implant body so as to not extend around an entire circumference of the implant body.

BRIEF DESCRIPTION OF THE DRAWINGS

The present invention is described in greater detail below on the basis of embodiments and of the drawings in which.

DETAILED DESCRIPTION

Figure 1:
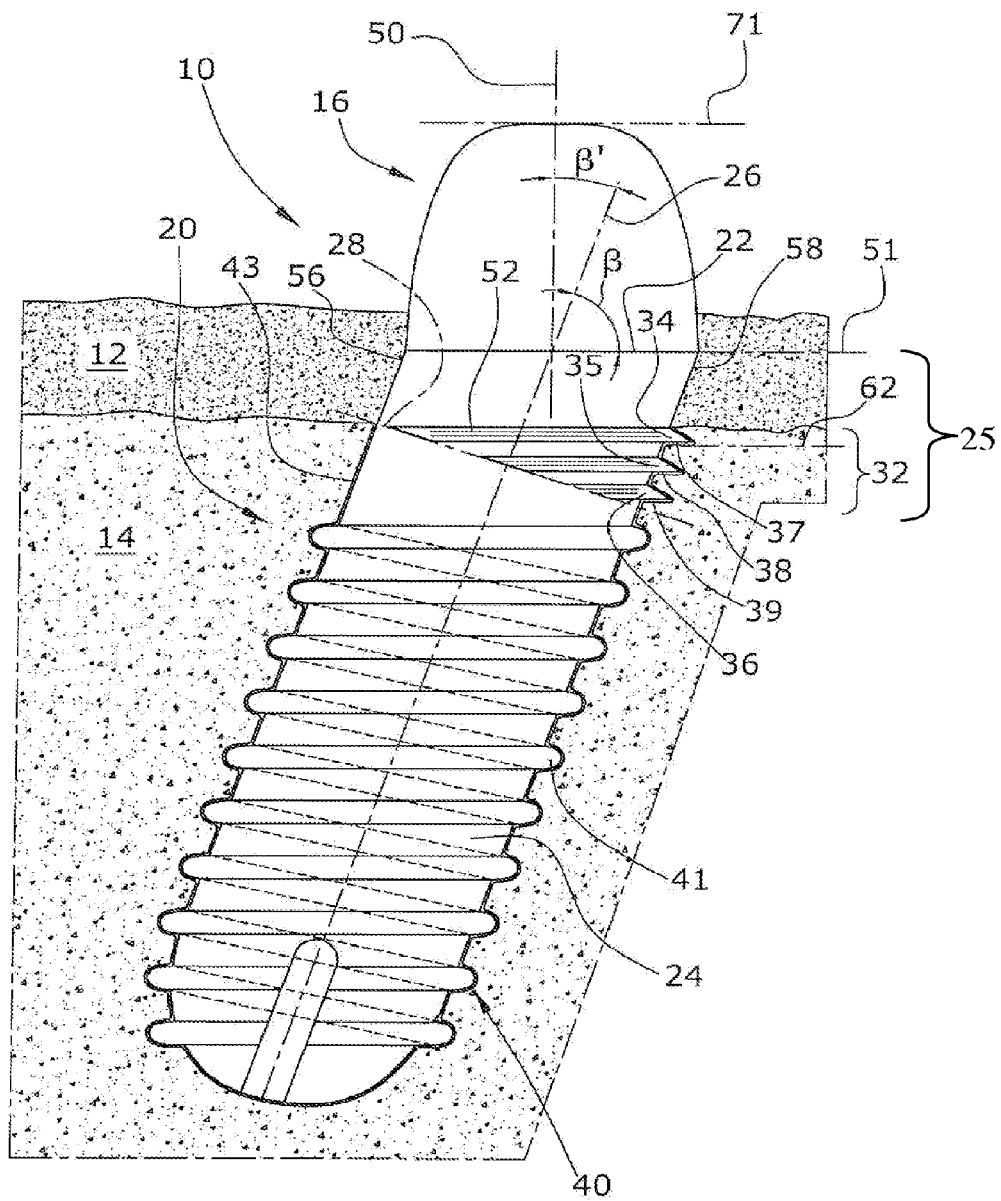
FIG. 1 shows a lateral view of a dental implant assembly comprising a jaw-mounted dental implant.

In an embodiment of the present invention, the jaw-mounted dental implant comprises an implant body which, on its longitudinal end facing away from the jaw, is provided with an implant-attachment fastening structure for fastening thereto the implant attachment. The implant attachment can be formed in one or two parts. The implant attachment can, for example, comprise a replacement-tooth neck portion which is fastened to the implant body and to which the replacement-tooth head portion is fixed, for example, by being cemented thereto.

On the longitudinal end of the implant body facing away from the jaw, the implant body comprises an implant attachment plane on which the implant attachment is supported. Said attachment plane extends at an angle $\beta$ of 75° to 45° relative to the longitudinal axis of the implant body. If the implant attachment has been seated on said attachment plane with its longitudinal axis oriented exactly vertically to the plane, the longitudinal axis of the implant attachment thus extends at an angle of 15° to 45° relative to the longitudinal axis of the implant body. Since the attachment plane is arranged at an inclination relative to the implant body, the introduction of force from the implant attachment into the implant body will occur substantially vertically to the attachment plane, under the precondition of a correct selection of the attachment angle and of the orientation of the attachment plane in space.

In an embodiment of the present invention, the implant body can, for example, comprise a bone portion which in the implanted state of the implant is entirely immersed into the jawbone, and a non-bone portion extending out of the jawbone and into the gingiva. On the longitudinal end of the implant-body bone portion facing away from the jaw, there is provided a support structure which projects radially outward from the outer surface of the implant body and which is formed by at least one support web arranged in a web plane. The support web is thus arranged in a single plane and does not describe a helical line. Said web plane is inclined relative to an implant-body transverse plane at the attachment angle $\beta$ so that the web plane is arranged substantially parallel to the attachment plane of the implant body.

The web plane of the support web is thus arranged substantially vertically to the longitudinal axis of the implant attachment so that the forces introduced via the implant attachment along its longitudinal axis can be introduced into the jawbone via the support webs arranged substantially vertically to said longitudinal axis, wherein said introduction of forces takes place substantially vertically to the web plane of the support webs. The areal forces introduced from the implant body into the jawbone can thereby be considerably reduced, which in turn considerably decreases the danger of bone deterioration.

In an embodiment of the present invention, the support web does not extend along the whole periphery of the implant body but is arranged only on that portion of the periphery of the implant body where the forces are introduced from the implant body into the jawbone. The support web is thus interrupted in the peripheral direction by an interruption region on the side of the obtuse angle of the implant body. The obtuse-angle side of the implant body is defined as that side on which the included angle between the outer surface and the attachment plane of the implant body is largest, i.e., where the outer angle is obtuse. The acute-angle side of the implant body is arranged exactly opposite to the obtuse-angle side, i.e., where the angle included between the outer surface and the attachment plane is smallest, i.e., where the outer angle is acute. By the interruption of the support web on the obtuse-angle side of the implant body, the total perimeter of the implant body at this side is kept as small as possible. This is important because the allowable total diameter of the implant body is limited and amounts to just a few millimeters.

In an embodiment of the present invention, the bottom side of the support web can, for example, be planar so as to extend substantially parallel to the web plane and/or the attachment plane. In this manner, there the largest possible force-transmission area is generated via which the introduced forces will be transmitted into the jawbone substantially vertically to the interface of the support web.

In an embodiment of the present invention, the support structure can, for example, be formed by a plurality of mutually parallel support webs. By suitable selection of the number of the support webs, the force-transmission area which is arranged substantially vertically to the force introduction, can be correspondingly enlarged.

In an embodiment of the present invention, the interruptions of the support webs in the peripheral direction can, for example, be of a different respective length from one support web to the next one. In this manner, each support web can be limited to that sector where a force transmission will really take place. The implant body is thereby strengthened in the regions where the interruption is provided.

In an embodiment of the present invention, the interruptions of the support webs can, for example, be respectively longer toward the longitudinal end facing toward the jaw than on the longitudinal end of the bone portion of the implant body facing away from the jaw. The farther the support web is located away from the attachment plane, the larger is the interruption sector and the smaller is the support web sector. The support webs can, for example, be arranged above each other centrosymmetrically, i.e., the center lines of the support webs extend in one single radial plane.

In an embodiment of the present invention, all interruptions of the support webs can, for example, extend at least on the jaw side of a transverse plane of the implant body. This transverse plane can, for example, intersect at a single point with the plane delimiting the bone portion of the implant body.

Most jaw-mounted dental implants comprise, in their bone portion, a thread structure for screwing the implant body into the jaw bone. When being implanted, the implant body will thus be screwed into the jawbone. In the process, it must be avoided that the support structure by its support webs might collide with the jawbone, since the support webs are not of a helical but of an annular configuration and describe a part of an ellipse. The support webs thus cannot be screwed into the jawbone. For this reason, a correspondingly wide bore must be drilled in the jawbone in that region thereof where the support webs are immersed into the jawbone. This drilled-open region can be filled out entirely by the support webs if these are interrupted on the jaw side in a transverse plane. Up to this transverse plane, the support structure formed by the support webs can be axially inserted or screwed into this drilled-open region.

In an embodiment of the present invention, the attachment fastening structure can, for example, comprise an inner cone whose cone axis is oriented substantially vertically to the web plane. This generally makes it possible to use linear implant attachments for linear implant assemblies.

In an embodiment of the present invention, the attachment fastening structure can, for example, comprise a flexible anchoring strand which extends in the implant body in the longitudinal direction of the implant body and is anchored therein. The larger the inclination of the implant attachment longitudinal axis relative to the implant body longitudinal axis is, the smaller is the depth in the implant attachment longitudinal axis which is available for fastening the implant attachment in the implant body. By providing a flexible anchoring strand, the whole longitudinal extension of the implant body can in principle be used for fixation. In the implant body, the anchoring strand runs in the longitudinal direction of the implant body, and, within the implant attachment, it runs in the longitudinal direction of the implant attachment. In the region of the fastening structure, the anchoring strand is correspondingly deflected by the attachment angle.

In an embodiment of the present invention, the jaw-mounted dental implant can, for example, be designed as a screw-type implant and comprises, in its bone portion, a thread structure for screwing the implant body into the jawbone.

Figure 2:
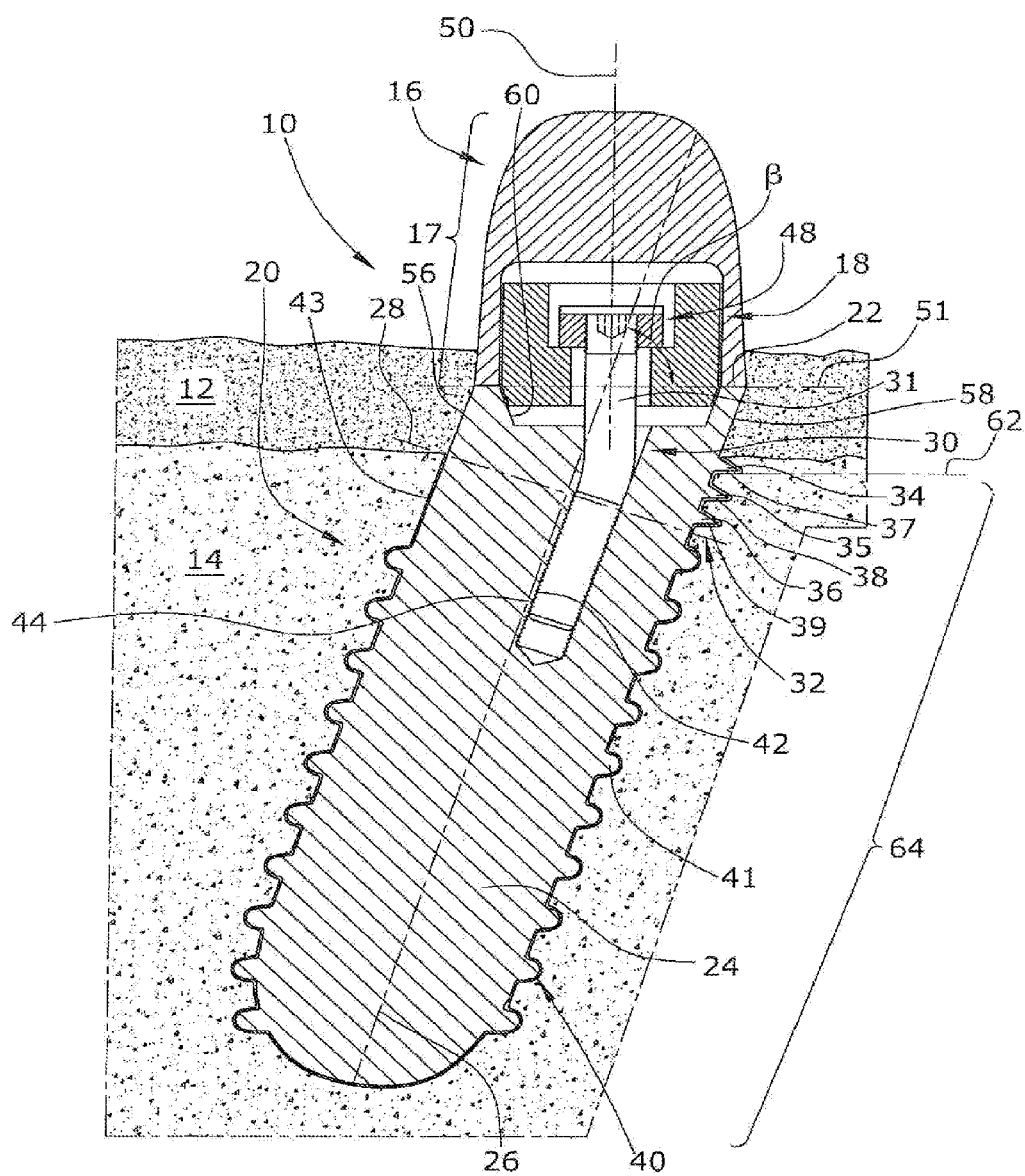
FIG. 2 shows a longitudinal sectional view of the dental implant assembly of FIG. 1.

FIGS. 1 and 2 schematically illustrate an angled jaw-mounted dental implant assembly 10 which has been implanted into a patient's jaw. In the situation depicted herein, the patient's jaw is a lower jaw and consists of the jawbone 14 and the gingiva 12. The jaw-mounted dental implant assembly substantially consists of three individual parts, notably the jaw-mounted dental implant 20 made of titanium, the replacement-tooth neck portion 18 made of titanium and fastened to said implant, and the replacement-tooth head portion 16 made of ceramic and in turn fastened to the replacement-tooth neck portion 18. The replacement-tooth neck portion 18 and the replacement-tooth head portion 16 together form an implant attachment 17.

The jaw-mounted dental implant 20 is formed by a one-pieced implant body 24 which is subdivided, depending to its environment, into a bone portion 64 and an adjoining gingiva portion. The gingiva portion terminates in an attachment plane 51 with the implant attachment 17 mounted thereon. The attachment plane 51 is arranged on the longitudinal end 22 of the implant body 24 facing away from the jaw. The implant body 24 has a longitudinal axis 26 arranged at an angle β of 15° to 45° relative to the longitudinal axis 50 of the implant attachment 17. From this, it results that the attachment plane 51 is arranged at an angle β of 75° to 45° relative to the longitudinal axis 26 of the implant body.

The bone portion 64 of implant body 24 is functionally divided into two portions, a portion facing toward the jaw having a thread structure 40 comprising a thread-shaped web 41 for screwing the implant body 24 into the jawbone 14, and a coronal end face 25 comprising a (in lateral view) wedge-shaped support structure 32 with a plurality of support webs 34,35,36 by which the end of implant body 24 facing away from the jaw is supported in the jawbone 14.

Said support webs 34,35,36 are arranged in a respective web plane 62, wherein all web planes of the support webs 34,35,36 are parallel to each other and parallel to the attachment plane 51. On their bottom sides 37,38,39 facing toward the jaw, all support webs 34,35,36 are planar, the planar bottom sides 37,38,39 being substantially parallel to the attachment plane 51 of implant body 24. The attachment plane 51 is substantially parallel to a virtual occlusal plane 71 extending between the lower jaw and the upper jaw of the patient.

On an obtuse-angle side 56 of implant body 24, the support webs 34,35,36, provided in a number of three in the present case, are interrupted by an interruption region in the circumferential direction. The obtuse-angle side 56 of implant body 24 is that point or side of implant body 24 where the angle formed by the implant body between its outer surface 43 and the attachment plane 51 is largest and is larger than 90°. The acute-angle side 58 is located exactly opposite to the obtuse-angle side 56. The support-web interruption is respectively provided on the jaw side of a transverse plane 28 of implant body 24. This transverse plane 28 extends vertically to the implant body longitudinal axis 26 and intersects at exactly one point with the interface between the jawbone 14 and the gingiva 12 and respectively with the plane separating the bone portion 64 and the gingiva portion of implant body 24. The interruption of the respective support web can extend, in case of a support web 34 facing toward the jaw, across a sector of, for example, 30° of the implant body 24 having a circular cross section, and, in case of a support web 36 facing away from the jaw, across distinctly more than 180°.

On its end facing away from the jaw, the implant body 24 comprises for use as an attachment fastening structure, in the region of the attachment plane 51, inter alia an inner cone 60 into which a corresponding outer cone of the replacement-tooth neck portion 18 is inserted. The replacement-tooth neck portion 18 is axially clamped to implant body 24 with the aid of a flexible anchoring strand 30. The anchoring strand 30 comprises a flexible anchoring strand body 31 which by its end-side outer thread 44 is screwed into a corresponding inner thread 42 within implant body 24. The other end of the anchoring strand body 31 is axially clamped to the replacement-tooth neck portion 18 by use of a clamping nut 48.

On the support webs 34,35,36, microgrooves 52 are provided in the longitudinal direction of the support webs for improving the osseointegration and the adherence of the jawbone 14 to the implant. Alternatively or additionally, the surface of the support webs 34,35,36 and of the other surfaces of implant body 24 can be structured or roughened by other measures so as to improve the adherence between the jawbone and the implant body.

The present invention is not limited to embodiments described herein; reference should be had to the appended claims.

What is claimed is:

1. A jaw-mountable dental implant comprising:
an implant attachment;
an implant body comprising:
    a longitudinal end configured to face away from a jaw,
    a coronal end face,
    a longitudinal axis,
    an obtuse-angle side,
    an implant body bone portion,
    an attachment plane arranged at the longitudinal end, the attachment plane being inclined at an attachment angle β of 75° to 45° relative to the longitudinal axis, and
    a support structure projecting outward from an outer surface of the implant body on the coronal end face, the support structure comprising at least one support web arranged in a web plane, the web plane being arranged substantially parallel to the attachment plane, wherein the at least one support web is interrupted by an interruption region arranged in a circumferential direction at the obtuse-angle side so as to not extend around an entire circumference of the implant body; and
an attachment fastening structure arranged in the implant body, the attachment fastening structure being configured to fasten the implant attachment on the longitudinal end,
wherein, the obtuse-angle side is a side of the implant body where an angle formed between the outer surface and the attachment plane of the implant body is larger than 90°.

2. The jaw-mountable dental implant as recited in claim 1, wherein each of the at least one support web includes a bottom side which is planar and which is arranged parallel to the web plane.

3. The jaw-mounted dental implant as recited in claim 1, wherein the support structure includes at least two support webs, wherein the at least two support webs are parallel to each other.

4. The jaw-mountable dental implant as recited in claim 3, wherein each of the at least two support webs includes interruptions, wherein the interruptions of the at least two support webs each have a different respective length.

5. The jaw-mountable dental implant as recited in claim 4, wherein the interruptions of the at least two support webs are configured so that an interruption arranged to face the jaw is respectively longer than an interruption arranged to face away from the jaw.

6. The jaw-mounted dental implant as recited in claim 4, wherein the interruptions extend on a jaw side of a transverse plane.

7. The jaw-mountable dental implant as recited in claim 1, wherein the attachment fastening structure includes an inner cone with a cone axis oriented substantially vertically to the web plane.

8. The jaw-mountable dental implant as recited in claim 1, wherein the attachment fastening structure includes a flexible anchoring strand which extends in the implant body in a longitudinal direction and is anchored in the implant body.

9. The jaw-mountable dental implant as recited in claim 1, wherein a jaw-side end of the implant body bone portion includes a thread structure configured to screw the implant body into a jaw bone.

10. A jaw-mountable dental implant comprising:
an implant attachment;
an implant body comprising:
    a longitudinal end configured to face away from a jaw,
    a coronal end face,
    a longitudinal axis,
    an obtuse-angle side,
    an implant body bone portion,
    an attachment plane arranged at the longitudinal end, the attachment plane being inclined at an attachment angle β of 75° to 45° relative to the longitudinal axis, and
    a support structure projecting outward from an outer surface of the implant body on the coronal end face, the support structure comprising at least one support web arranged in a web plane, the web plane being arranged substantially parallel to the attachment plane, wherein the at least one support web is interrupted by an interruption region arranged in a circumferential direction at the obtuse-angle side so as to not extend around an entire circumference of the implant body; and an attachment fastening structure arranged in the implant body, the attachment fastening structure being configured to fasten the implant attachment on the longitudinal end, wherein, the obtuse-angle side is a side of the implant body where an angle formed between the outer surface and the attachment plane of the implant body is larger than 90°, and wherein, each of the at least one support web includes a bottom side which is planar and which is arranged parallel to the web plane.

11. The jaw-mounted dental implant as recited in claim 10, wherein the support structure includes at least two support webs, wherein the at least two support webs are parallel to each other.

12. The jaw-mountable dental implant as recited in claim 11, wherein each of the at least two support webs includes interruptions, wherein the interruptions of the at least two support webs each have a different respective length.

13. The jaw-mountable dental implant as recited in claim 12, wherein the interruptions of the at least two support webs are configured so that an interruption arranged to face the jaw is respectively longer than an interruption arranged to face away from the jaw.

14. The jaw-mounted dental implant as recited in claim 12, wherein the interruptions extend on a jaw side of a transverse plane.

15. The jaw-mountable dental implant as recited in claim 10, wherein the attachment fastening structure includes an inner cone with a cone axis oriented substantially vertically to the web plane.

16. The jaw-mountable dental implant as recited in claim 10, wherein the attachment fastening structure includes a flexible anchoring strand which extends in the implant body in a longitudinal direction and is anchored in the implant body.

17. The jaw-mountable dental implant as recited in claim 10, wherein a jaw-side end of the implant body bone portion includes a thread structure configured to screw the implant body into a jaw bone.

\* \* \* \* \*